United States Patent [19]

Craig et al.

[11] Patent Number: Plant 7,350

[45] Date of Patent: Oct. 9, 1990

[54] GERANIUM PLANT "MISTY"

[75] Inventors: Richard Craig; Leon Glicenstein, both of State College, Pa.

[73] Assignee: Research Corporation Technologies, Inc., Tucson, Ariz.

[21] Appl. No.: 347,102

[22] Filed: May 3, 1989

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Scully, Scott, Murphy & Presser

[57] ABSTRACT

A continuous blooming, compact, self branching geranium plant having large, showy, predominantly red-purple floret clusters, and excellent tolerance to high heat and low light conditions.

1 Drawing Sheet

The present invention relates to a new and distinct cultivar of geranium (*Pelargonium*×*hortorum*) called "Misty". The cultivar is particularly well adapted to both commercial greenhouse production and garden performance. The cultivar is early flowering, floriferous, self-branching and compact.

The cultivar was developed from an organized, scientifically designed breeding program carried out at the Department of Horticulture, The Pennsylvania State University, University Park, Pa. 16802. The breeding program was designed to create new geranium genotypes with clear, bright colors which combined the flowering ability and compactness of European cultivars with the heat tolerance, low light tolerance and excellent greenhouse production qualities of cultivars developed at Penn State. The pedigree of this cultivar is as follows:

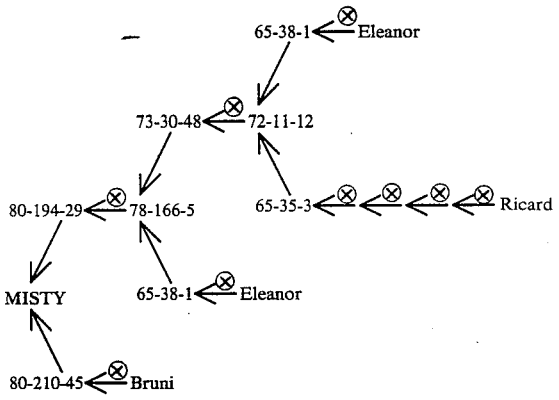

The selection was asexually propagated by cuttings and the reproductions ran true.

With reference to the detailed description of the cultivar which follows, the test plant was grown in a glasshouse under full natural light, at a night temperature of approximately 58° F., and a day temperature of approximately 68° F. Soilless medium was fertilized with every watering with 200 ppm nitrogen from 15-16-17.

BRIEF DESCRIPTION OF THE DRAWING

The sheet of drawing illustrates, in color, the short habit of the plant and the presentation of predominantly red-purple floret clusters carried well above attractively zoned and densely foliated plants.

Color readings were taken under incandescent light at 200 foot candles and color identification was by reference to The Royal Horticultural Society Colour Charts, except where common terms of color definition are employed.

THE PLANT

Classification

*Botanical.*—*Pelargonium*×*hortorum.*

*Tradename.*—#818-(82-125-3)='Misty'.

Form: Compact, self-branching.

Height: 16.75 cm; range 15.0–20.0 cm.

Growth: Free branching from base; short internodes.

Leaves:

*Size.*—Largest measured 6.5 cm long×10.5 cm wide; ratio of length to width approximately 2:3.

*Shape.*—Reniform, variously lobed.

*Margin.*—Crenate.

*Texture.*—Pubescent; dull.

*Color.*—Adaxial: Distal: Green 137A. Zone: Greyed-purple 187A overlaid with green 137A. Proximal: Green 137A. Abaxial: Yellow-green 147B.

*Ribs and veins.*—Palmate venation; veins recessed and prominent.

Petioles:

*Length.*—Up to 9.2 cm.

*Color.*—Green 144A.

Stem:

*Internode length.*—Up to 1.5 cm.

*Color.*—Green 144A.

THE FLOWER

Blooming habit: Continuous.

Inflorescence form: Umbellate.

Inflorescence size: Depends on number of florets; inflorescences often 10.0 cm across.

Persistence: Persistent, non-shattering.

Disease resistance: Not known; favorable in outdoor trials.

Lasting quality: Excellent, usually 3 weeks or longer.

Florets:

*Number.*—Often over 40 per inflorescence.

*Form.*—Cupped.

*Size.*—2.5–3.5 cm across open floret.

Petals:

*Number.*—5–9.

*Texture and appearance.*—Smooth to slightly wrinkled.

*Color.*—Upper petals: Adaxial: Distal two-thirds: Red-purple 57C. Proximal one-third: White 155D with veins red-purple 57C. Abaxial: Distal margin: Red-purple 57C. Center: Red-purple 62A with veins red-purple 57C. Base: White group 155D. Lower petals: Adaxial: Distal two-thirds: Red-purple 57C. Proximal one-third: Red 55B with veins red-purple 57C. Base: Small area of white 155D.

Petaloids:

*Number.*—None observed.

Sepals:

*Number.*—5–9.

*Pedicel.*—Length: 2.2–3.1 cm. Color: Green 144A.

Peduncle: Arises from node; opposed to leaf petiole; thick (3–5 mm diameter); lightly pubescent.

*Length.*—12.0 cm (average).

*Color.*—Green 144A.

REPRODUCTIVE ORGANS

Androecium:

*Stamens.*—Up to 11 flat, ribbon-like filaments with rose-purple tips, joined at their bases; versatile attachment to anthers which are purple and well-developed; 2 sizes of pollen: larger grains are pale orange in color, smaller grains are dark orange in color.

*Staminodes.*—1–3 flat, ribbon-like filaments with no anthers.

*Petaloid stamens.*—1–2 petal-like filaments with partially developed anthers.

Gynoecium:

*Pistil number.*—1.

*Length.*—5.5–9.5 mm.

*Stigma.*—4–5-parted; light purple.

*Style.*—1.0–2.0 mm long; green.

*Ovary.*—4–5-parted; superior; very pubescent.

*Fruit.*—Achene schizocarp; rarely observed.

What is claimed is:

1. A new and distinct cultivar of Geranium substantially as illustrated and described, characterized as being particularly well adapted to both commercial greenhouse production as well as garden performance, and as being early flowering, floriferous, self-branching, compact, heat-tolerant and low-light-tolerant.

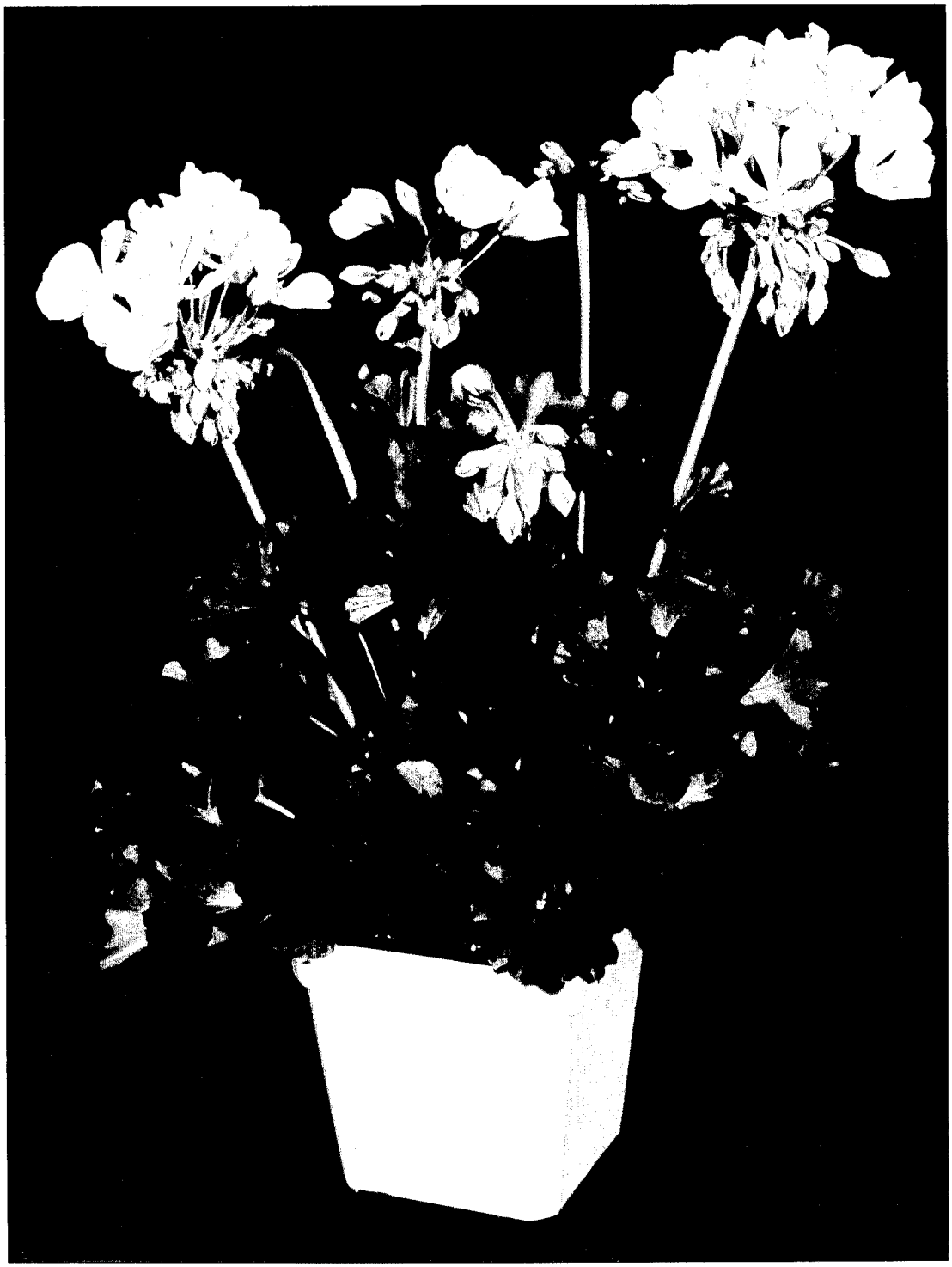

* * * * *